United States Patent
Bovina et al.

(10) Patent No.: US 6,261,796 B1
(45) Date of Patent: Jul. 17, 2001

(54) METHOD AND KIT FOR MEASURING MITOCHONDRIAL ACTIVITY

(75) Inventors: Carla Bovina; Giorgio Lenaz; Sante Tura, all of Bologna; Lucia Catani, Faenza; Milena Merlo Pich, Bologna, all of (IT)

(73) Assignee: Universita' Degki Studi di Bologna (IT)

( * ) Notice: Subject to any disclaimer, the term of this patent is extended or adjusted under 35 U.S.C. 154(b) by 0 days.

(21) Appl. No.: 09/550,013

(22) Filed: Apr. 14, 2000

(30) Foreign Application Priority Data

Apr. 20, 1999 (IT) .............................. BO99A0185

(51) Int. Cl.[7] .............................. C12Q 1/02; C12Q 1/54; C12Q 1/00
(52) U.S. Cl. .............................. 435/29; 435/14; 435/975; 435/4
(58) Field of Search .............................. 435/29, 14, 975, 435/4

(56) References Cited

FOREIGN PATENT DOCUMENTS

1046714 A2 * 10/2000 (EP) .

OTHER PUBLICATIONS

Lenaz et al; "Mitochondria Oxidative Stress, and Antioxidant Defences; Acta Biochimica Polonica"; Warszawa, PO vol. 46, No. 1;Mar. 30, 1999, pp. 1–21, month not availble.*
Holmsen; "Biochemistry of the Platelet: Energy Metabolism"; Lippincott, Philadelphia; 1987 pp. 631–643, month not available.*
Makler et al; "Measurement of the Lactate Dehydrogenase Activity of Plasmodium Falciparum as an assessment of Parasitemia"; American Journal of Tropical Medicine and Hygiene; vol. 48, No. 2 1993; pp. 205–210, month not available.*
Sajko et al; "Administration of Lactate Dehydrogenase From the Ox Heart to Determine the Content of Pyruvate in Milk"; Medycyna Weterynary JNA, vol. 41, No. 7, 1985 pp. 442–444, month not available.*
Homyk et al; "Steady–Stae Kinetics and the Inactivation by 2 3 Butanedione of the Energy Independent Transhydrogenase of *Escherichia–Coli*Cell Membranes"; Biochimica et Bioiphysica ACTA; vol. 571, No. 2, 1979, pp. 201–217, month not available.*
Holmsen; "Hydrogen Peroxide Lowers ATP Levels in Platelets without Altering Adenylate Energy Charge and Platelet Function"; Journal of Biological Chemistry; Vol 52, No. 5, 1977; pp. 1752–1757.*
Holmsen; "Effects of Antimycin A and 2–Deoxyglucose on Secretion in Human Platelets;Differential Inhibition of the Secretion of Acid Hydrolases and Adenine Nucleotides"; Biochemical Journal; Vol 192, No. 2; 1979; pp. 413–420.*

* cited by examiner

Primary Examiner—Louise N. Leary
(74) Attorney, Agent, or Firm—Nixon & Vanderhye PC (57) ABSTRACT

The present invention relates to a method for measuring mitochondrial activity by measuring platelet A lactate. The present invention also relates to a new method for dosing the quantity of platelet lactate using the chromogenic agent 3-acetyl-pyridine-$NAD^+$ and the ox heart LDH enzyme. The present invention also relates to a diagnostic (micromethod) kit.

20 Claims, 7 Drawing Sheets

|  | Ctl | AA | DOG | Δ lactate (AA-Ctl) = mitochondrial ATP | Δ lactate (Ctl - DOG) = glycolytic ATP | mit ATP/glyc ATP |
|---|---|---|---|---|---|---|
|  | | | | μmol / min / $10^{11}$ cells | | |
| young (5) | 1.44 ± 0.25 | 3.86 ± 0.36 | 1.18 ± 0.22 | 2.42 ± 0.24 | 0.26 ± 0.11 | 11.76 ± 6.87 |
| elderly (6) | 1.97 ± 0.90 | 3.98 ± 0.94 | 1.63 ± 0.88 | 2.02 ± 0.20 | 0.37 ± 0.10 | 5.93 ± 1.95 * |

FIG.1

| | Ctl | AA | DOG | Δ lactate (AA-Ctl) = mitochondrial ATP | Δ lactate (Ctl - DOG) = glycolytic ATP | mit ATP/glyc ATP |
|---|---|---|---|---|---|---|
| | | | | µmol / min / $10^{11}$ cells | | |
| young (5) | 1.44 ± 0.25 | 3.86 ± 0.36 | 1.18 ± 0.22 | 2.42 ± 0.24 | 0.26 ± 0.11 | 11.76 ± 6.87 |
| elderly (6) | 1.97 ± 0.90 | 3.98 ± 0.94 | 1.63 ± 0.88 | 2.02 ± 0.20 | 0.37 ± 0.10 | 5.93 ± 1.95 * |

FIG. 2

| Treatment | Lactate<br>($\mu mol$ / min. $10^{11}$ cells) |
|---|---|
| control (=glycolytic ATP) | 0.18 |
| + AA | 4.57 |
| $\Delta$ lactate (=mitochondrial ATP) | 4.39 |

$$\frac{\text{mitochondrial ATP}}{\text{glycolytic ATP}} = \frac{4.39}{0.18} = 24.4$$

Glucose flow during anaerobic glycolysis 0.18 : 2*    =0.09 $\mu mol$ / min $10^{11}$ cells    (43 %)

4.39 : 36**    =0.12 $\mu mol$ / min $10^{11}$ cells    (57 %)

\*   ATP/glucose yield from anaerobic glycolysis
\*\*  Average ATP/glucose yield through oxidative phosphorylation

FIG. 3

| | Ctl | AA | Δ lactate (AA-Ctl) | Ctl | AA | Δ lactate (AA-Ctl) | mit ATP/glyc ATP |
|---|---|---|---|---|---|---|---|
| | | mg/dl | | | lactate µmol/min./10$^{11}$ cells | | |
| young (26) | 1.58 ± 0.97 | 14.84 ± 3.80 | 13.26 ± 4.08 | 0.45 ± 0.28 | 4.18 ± 1.04 | 3.73 ± 1.19 | 26.46 ± 57.94 |
| elderly (26) | 2.67 ± 2.35 | 11.36 ± 3.33 | 8.69 ± 3.54 | 0.85 ± 0.78 | 3.47 ± 0.85 | 2.62 ± 0.89 | 5.41 ± 4.94 |
| p= | 0.04 | 0.001 | 0.00007 | 0.021 | 0.009 | 0.0002 | 0.089 |

50 · 10⁶ cells per test

| Time | Ctl | AA | Δ lactate (AA-Ctl) | Ctl | AA | Δ lattato (AA-Ctl) |
|---|---|---|---|---|---|---|
| min. | µg/ml * | µg/ml * | µg/ml | lactate µmol/ min./10¹¹ cells | lactate µmol/ min./10¹¹ cells | lactate µmol/ min./10¹¹ cells |
| 30  | 1.3 | 5.6  | 4.3  | 0.48 | 2.07 | 1.59 |
| 90  | 3.1 | 14.7 | 11.6 | 0.38 | 1.81 | 1.43 |
| 120 | 4.6 | 24.2 | 19.6 | 0.43 | 2.24 | 1.81 |
| 150 | 6.0 | 30.2 | 24.2 | 0.44 | 2.24 | 1.80 |
| 180 | 6.7 | 34.0 | 27.3 | 0.41 | 2.09 | 1.68 |

FIG. 7B

100 · 10⁶ cells per test

| Time | Ctl | AA | Δ lactate (AA-Ctl) | Ctl | AA | Δ lactate (AA-Ctl) |
|---|---|---|---|---|---|---|
| min. | µg/ml* | µg/ml* | µg/ml | lactate µmol/ min./$10^{11}$ cells | lactate µmol/ min./$10^{11}$ cells | lactate µmol/ min./$10^{11}$ cells |
| 30 | 1.3 | 16.0 | 14.7 | 0.24 | 2.96 | 2.72 |
| 45 | 0.0 | 20.4 | 20.4 | 0.00 | 2.52 | 2.52 |
| 60 | 0.7 | 28.9 | 28.2 | 0.06 | 2.67 | 2.61 |
| 90 | 2.6 | 41.9 | 39.3 | 0.16 | 2.58 | 2.42 |
| 120 | 6.9 | 50.4 | 43.5 | 0.32 | 2.33 | 2.01 |
| 150 | 8.9 | 68.9 | 60.0 | 0.33 | 2.55 | 2.22 |
| 180 | 10.8 | 77.9 | 67.1 | 0.33 | 2.40 | 2.07 |

\* Values obtained after subtraction of the blank at zero time (µg/ml)

METHOD AND KIT FOR MEASURING MITOCHONDRIAL ACTIVITY

BACKGROUND OF THE INVENTION

The present invention relates to a method for measuring mitochondrial activity. Moreover, the present invention relates to a diagnostic kit for measuring platelet mitochondrial activity.

As is known, Reactive Oxygen Species (ROS) play a fundamental role in pathological processes. Their chemical aggression towards all biological macromolecules causes a deterioration in cell structures which has been suggested to be the cause or pathogenic event leading to many degenerative diseases, cancer and ageing. In order to understand ROS biochemistry and pathology, research focuses chiefly on mitochondrions, since these are important ROS producers in the respiratory chain and are particularly vulnerable in the sophisticated mechanism of oxidative phosphorylation. The mitochondrial ageing theory is based on the idea that cells which are constantly exposed to ROS are gradually damaged, particularly through random errors in the mitochondrial DNA, in their energy functions, with a gradual loss of efficiency and consequent cell death.

In light of the above, ageing and age-related illnesses in humans must take into account mitochondrial activity. This activity can be directly investigated only in cells containing mitochondria, for example platelets. Blood platelets are a particularly suitable system, since the platelets contain mitochondria and are easily collected using a non-invasive technique.

As is known, platelets obtain the energy which allows them to function partly from glycolysis and partly from mitochondrial oxidative phosphorylation. The most important function is the aggregation process, part of the blood coagulation mechanism, and physiologically a result of stimulation and exocytosis of their secretion granules. The aggregation of platelets requires energy, conserved in the form of ATP generated by both the glycolysis and the oxidative phosphorylation. Inhibition of the respiratory chain partially inhibits platelet aggregation, indicating that the function is mainly, but not completely, provided with energy by the glycolytic ATP.

Therefore, a method is still required for measuring mitochondrial activity. In particular, a method is required for measuring the mitochondrial activity using platelets. More specifically, a method is required for measuring mitochondrial activity by measuring the amount of glycolytic and mitochondrial ATP in the platelets.

The use of platelets as markers for mitochondrial lesions is due to the fact that the alterations which accompany ageing and age-related illnesses are present in all cells and, therefore, platelets can indicate general bioenergetic changes.

SUMMARY OF THE INVENTION

One aim of the present invention is to provide a method for measuring mitochondrial activity.

Another aim of the present invention is to provide a method for measuring mitochondrial activity using platelets.

Another aim of the present invention is to provide a method for measuring mitochondrial activity by measuring the amount of glycolytic and mitochondrial ATP in the platelets.

Yet another aim of the present invention is to provide a bioenergetic marker (biomarker) for mitochondrial activity which is an individual and customised indicator of biological age.

Another aim of the present invention is to provide a biomarker for mitochondrial activity which is an indicator of a tendency towards those illnesses which accompany ageing through mitochondrial activity.

Another aim of the present invention is to provide a biomarker for mitochondrial activity which is a diagnostic and prognostic indicator of any pathology involving altered mitochondrial activity.

Another aim of the present invention is to provide an indicator for evaluating the preservation of bags containing blood for transfusions.

The final but no less important aim of the present invention is to provide a diagnostic kit (micromethod) for measuring platelet mitochondrial activity.

These aims and others are which are described in the detailed description which follows were achieved by the Applicant, who developed a method for measuring mitochondrial activity by measuring the amount of platelet $\Delta$ lactate.

The present invention also relates to a diagnostic kit (micromethod) for measuring platelet mitochondrial activity by measuring the amount of platelet $\Delta$ lactate.

The basic characteristics of the above-mentioned method and kit are defined in the main claims; some special preferred embodiments of the invention, which do not limit the scope of its application, are described in the secondary claims.

The method for measuring mitochondrial activity which is the subject matter of the present invention uses inhibition of the mitochondrial respiratory chain by means of inhibitor agents in such a way as to obtain a measurement of the amount of glycolytic and mitochondrial ATP through the so-called Pasteur effect.

The amount of mitochondrial ATP (mitATP) is equal to the $\Delta$ lactate (lactate produced by the platelets inhibited with mitochondrial chain inhibitors minus the lactate produced by the uninhibited platelets (Ctl)).

The amount of glycolytic ATP (glycATP) is equal to the $\Delta$ lactate (lactate produced by the uninhibited platelets (Ctl) minus the lactate produced by the platelets inhibited with the glycolysis inhibitors).

The effective oxidation of the glycolytic pyruvate through the Krebs cycle and respiratory chain leads to the formation of low or zero levels of lactate through the action of the cytosolic lactate dehydrogenase on the pyruvate. In contrast, a reduced or ceased mitochondrial activity leads to a reduction in the lactate pyruvate by the excess reducing force exerted by the NADH formed by the glycolysis; at the same time, glycolysis is stimulated with the aim of maintaining the ATP production constant over time. Since, in the absence of mitochondrial activity, glycolysis produces two ATP molecules and two lactate molecules for each glucose molecule broken down, the stimulation of lactate production when the mitochondria are inhibited, is equivalent to the mitochondrial ATP production when subjected to inhibition.

The Applicant has discovered a relationship between the $\Delta$ lactate (more lactate is produced when the mitochondria are inhibited) and different categories of individuals. The Applicant found that there is less $\Delta$ lactate in the platelets of elderly individuals than in those of young individuals, demonstrating that there is a change in the mitochondrial energy in the platelets of elderly subjects and that platelets are a useful material for investigation, on which to use a mitochondrial marker.

The $\Delta$ lactate may be expressed as: $\Delta$ lactate=(AA−Ctl) where AA=lactate produced by platelets in the presence of specific respiratory chain inhibitors; Ctl=lactate produced by platelets in the absence of specific inhibitors.

The Applicant found it useful to use particular specific inhibitors, such as antimycin A to inhibit platelet aggregation. The inhibited respiratory chain produces less ATP and, as a result, the reduced amount of ATP produced reduces platelet aggregation.

BRIEF DESCRIPTION OF THE DRAWINGS

The description of some embodiments of the present invention refers to the accompanying drawings, in which.

DESCRIPTION OF THE PREFERRED EMBODIMENTS

The method which is the subject matter of the present invention was perfected on a sample of male and female subjects (donors) who did not suffer from systemic or haematological illnesses. The donors were not subjected to any pharmacological treatment which might interfere with platelet activity (for example, acetyl-salicylic acid and/or its derivatives). The donors selected were young persons aged between 18 and 30 (control group) and elderly individuals aged between 65 and 102. All operations involved the use of silicone glass or plastic laboratory equipment, to prevent platelet aggregation. Before taking blood from the vein, preferably without the use of a tourniquet, all donors were allowed to rest for at least 30 minutes.

The volume of blood taken was preferably between 3 and 20 ml. The blood was preferably taken using a syringe containing 0.5–5 ml of a buffer selected for example from the trisodium citrate and citric acid buffers. The blood taken was subjected to an initial separation. The blood samples taken from the donors were preferably centrifuged at around 300 g (where g is the gravity acceleration 9.81 m/s$^2$) for a time of between 5 and 15 minutes at a temperature of between 18 and 25° C. The centrifuged sample contains a fraction at the top, called the supernatant, and a fraction at the bottom containing a pellet of red corpuscles. The supernatant comprises a platelet-rich plasma (PRP).

The initial separation separates a platelet-rich plasma (PRP) from the blood sample.

After removing the PRP, the number of platelets which it contains is determined in a Cell Counter. Contamination with white and red corpuscles in the samples proved to be minimal.

The PRP obtained as indicated above was preferably divided into various parts with a volume of between 0.2 and 1 ml. The PRP was subjected to an initial incubation both in the presence of and in the absence of inhibitor agents. The length of the initial incubation is preferably between 2 and 4 hours, for example in a water bath with thermostat control, at a temperature of between 25 and 40° C., or even better, between 30 and 38° C. The inhibitor agents used by the Applicant are specific inhibitor agents and were selected from rotenone, potassium cyanide, antimycin, oligomycin, preferably using antimycin A to inhibit the respiratory chain at a common stage at the entry of all physiological substrates.

Upon completion of said initial incubation, the PRP samples incubated with and without inhibitor agents were subjected to a second separation. The PRP was preferably centrifuged at 1500 g for between 5 and 20 minutes at a temperature of between 18 and 25° C. The centrifuged sample comprises a fraction at the top, called the PPP (platelet-poor plasma) supernatant, and a fraction at the bottom comprising the platelets. The PPP supernatant contains the lactate produced by the platelets during the initial incubation.

The second separation separates out the lactate produced by the platelets during the initial incubation from the platelet-rich plasma (PRP).

The lactate obtained by the second separation was dosed. The top, supernatant PPP portions can either be used directly for dosing the lactate or can be preserved at a temperature of around minus 80° C. The supernatant PPP portions are thawed as required and the lactate dosed. Lactate dosing may be effected using any method known on the market.

The Applicant has identified a method for measuring the lactate, which can substitute or may be used as an alternative to those methods for measuring lactate available on the market.

Another aim of the present invention is to provide a spectrophotometric method for measuring lactate, using 3-acetyl-pyridine-NAD$^+$ as the chromogenic agent. 3-acetyl-pyridine-NAD$^+$ possesses a molar extinction coefficient $\epsilon=9.1$ mM$^{-1}$ cm$^{-1}$.

The method for measuring the lactate which is the subject matter of the present invention is based on the following reaction:

Lactate+3-acetyl-pyridine-NAD$^+$→Pyruvate+3-acetyl-pyridine-NADH+H$^+$

The enzyme LDH may be selected from those enzymes known on the market. The enzyme LDH is preferably ox heart. The 3-acetyl-pyridine-NADH has a maximum absorbance of $\lambda=363$ nm.

The method for measuring lactate proposed by the Applicant is different to the known methods on the market because it allows greater sensitivity in the entire field of lactate concentrations of diagnostic interest. In particular, the method which forms the subject matter of the present invention is especially recommended for measuring low concentrations of lactate, since the present method is more sensitive than the known methods when dealing with low concentrations.

The production of low concentrations of lactate by the platelets can be obtained by reducing the length of the initial platelet incubation while maintaining the number of platelets unchanged; or reducing the number of platelets incubated but leaving the length of the initial incubation unchanged. The high sensitivity of the method for measuring the lactate presented by the Applicant allows the lactate measurement to be made more rapidly and/or allows a reduction in the number of platelets to be incubated. The reduction in the number of platelets to be incubated is matched by a reduction in the amount of blood to be taken from the donor patient.

The method for measuring mitochondrial activity which is the subject matter of the present invention relates the Δ lactate measurement to the mitochondrial activity.

When the lactate measurement lies within a very low concentration range, for example between 0 and 15 micrograms/ml, the lactate originating from the plasma should preferably be removed. This disadvantage has been overcome by the Applicant, who has perfected a method for washing the platelets.

The subject matter of the present invention also includes a method for washing the platelets which can be implemented during separation of the platelets from the other blood cells.

The above-mentioned washing method is valid for precision dosing of the low levels of lactate produced during the incubation period.

The method for measuring mitochondrial activity which forms the subject matter of the present invention envisages at least one wash; for example, following the initial separation and before the initial incubation.

If necessary, the wash may be followed by a third separation before the first incubation. For example, the PRP sample from the first incubation was diluted with a washing solution to a ratio of between 1:0.5 and 1:5. The washing solution should contain NaCl, Tris/HCl (pH 7.4), Na-EDTA and glucose. The PRP diluted with the washing solution was subjected to the third separation by centrifuging at 1500 g for between 5 and 20 minutes. The centrifuging produced a pellet of platelets at the bottom, which was suspended in the same washing solution again. The third separation separates a pellet of platelets at the bottom from a supernatant consisting of the reject washing solution. Following the platelet washing stage, the method continues with the same operations as described above.

Inclusion of the platelet wash eliminates the plasma lactate, resulting in a more precise and sensitive measurement of the lactate in low concentration samples. It also reduces the incubation time, thanks to the fact that small differences in the lactate concentration are noticeable after eliminating the high levels of plasma lactate which contaminated the unwashed platelets.

Figure 1:
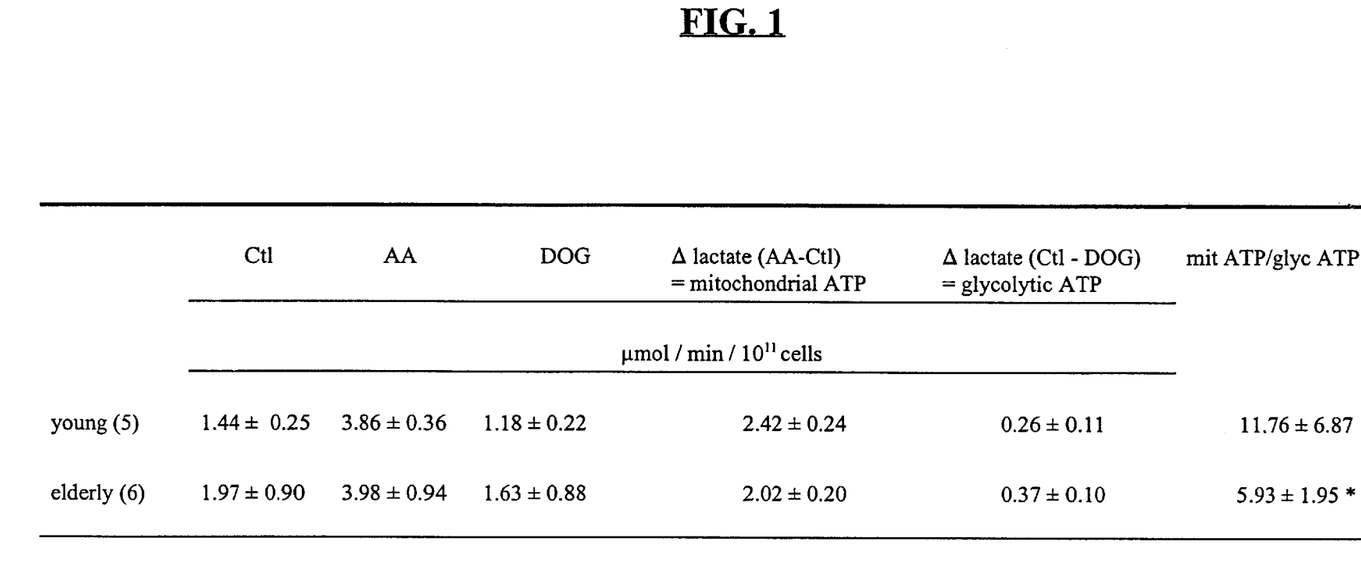
FIG. 1 is a table indicating the production of lactate in the platelets of young and elderly subjects in the presence of AA and DOG inhibitors.

The Applicant conducted a first study which aimed to measure the Δ lactate in human platelets taken from young and elderly individuals in the presence of the inhibitors AA (antimycin A, respiratory chain inhibitor) and DOG (deoxyglucose, glycolysis inhibitor) and incubated for 3 hours without prior washing. The results are shown in FIG. 1 and are expressed as mean ± standard deviation after 180 minutes of incubation, with the number of individuals indicated in brackets. In FIG. 1, Ctl=lactate produced by platelets without inhibitor AA; AA=lactate produced by platelets with inhibitor AA; DOG=lactate produced by platelets with inhibitor DOG and mitochondrial ATP/glycolytic ATP=Δ lactate (AA−Ctl)/Δ lactate (Ctl−DOG). The results indicate that the addition of AA causes an increase in lactate both in the young and in the elderly, compare column AA and column Ctl. The results indicate a significant difference between the mitochondrial ATP/glycolytic ATP ratio in the young and in the elderly (p<0.025).

Moreover, FIG. 1 reveals the need to subtract the basic value of the plasma lactate present in the cells before incubation. The values 1.44±0.25 and 1.97±0.90 are too high because they include the plasma lactate contamination. (Notice that despite contamination by the plasma lactate, the values 11.76 and 5.93 relative to mitochondrial ATP/glycolytic ATP are significant, but the values 2.42 and 2.02 relative to the Δ lactate (AA−Ctl) are incorrect due to the plasma lactate contamination. For this reason, incubation must also be carried out in the presence of the glycolytic inhibitor, for example deoxyglucose (DOG), in order to inhibit basic glycolysis and evaluate the basic lactate level. As already described, the Applicant has perfected a method for washing the platelets. This method allows the total elimination of the plasma lactate, which is not newly produced, so that even the low levels of lactate produced in the absence of antimycin A can be precisely dosed.

Figure 2:
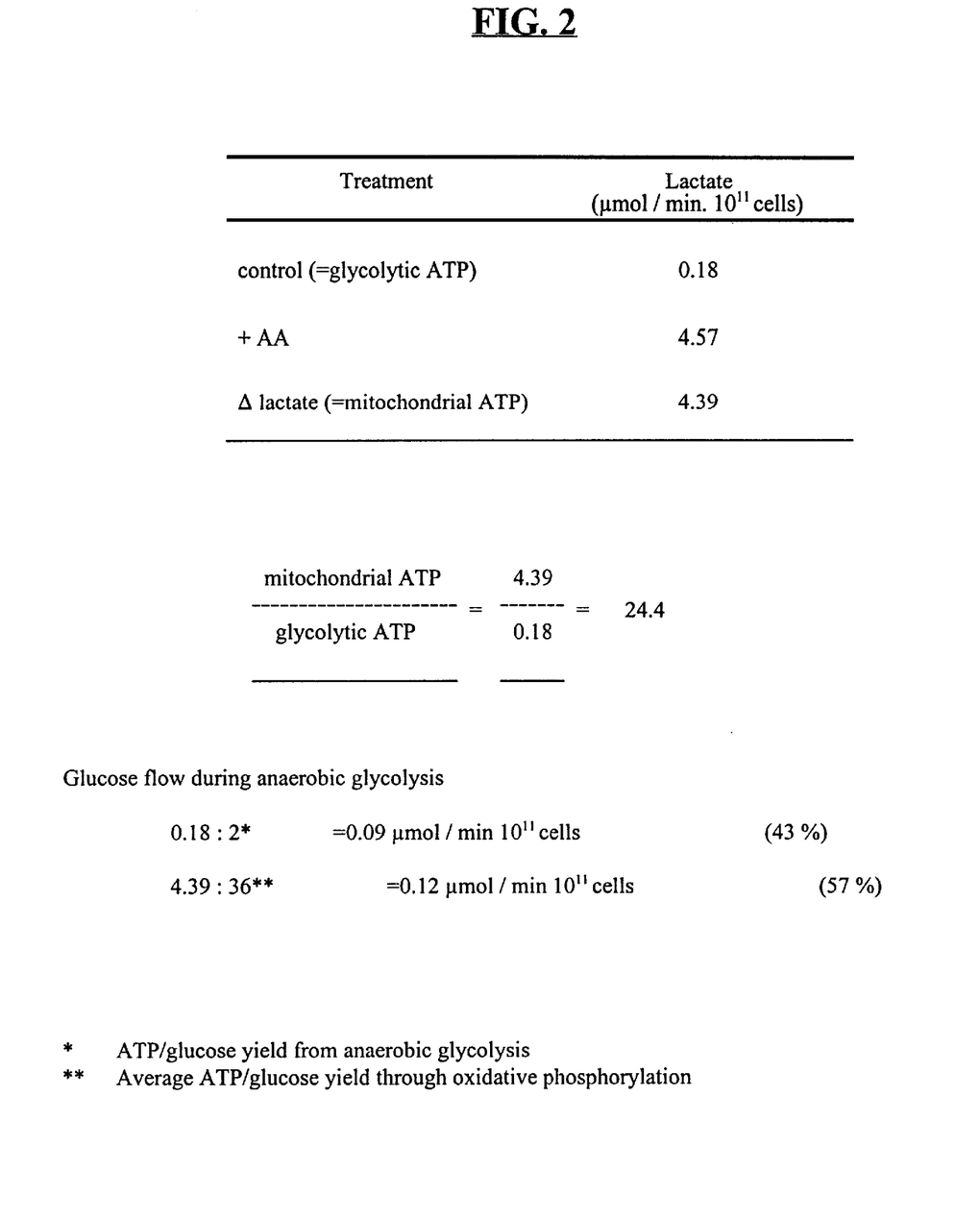
FIG. 2 is a table indicating the production of lactate in the washed platelets of a young individual.

The Applicant conducted a second study with the aim of measuring the Δ lactate in human platelets taken from young individuals, washed and incubated with and without antimycin A. The data in FIG. 2 shows that lactate production, which was quite low under basic conditions (see glycolytic ATP=0.18), was stimulated to around 25 times that figure following incubation with the inhibitor. These parameters may be used to calculate the difference between the basic glycolytic lactate and the figure following inhibition (Δ lactate=4.39) and the relative Δ lactate/basic lactate ratio: the latter represents the mitochondrial ATP/glycolytic ATP=24.4 ratio. The data in FIG. 2 confirms that the ATP yield, attributable to phosphorylation at the substrate level in glycolysis and to oxidative phosphorylation in the mitochondrial respiratory chain, can be used to calculate that under basic conditions the flow of glucose through oxidative phosphorylation is more than 60% of the entire metabolic flow, whilst less than 40% is interrupted at pyruvate level with lactate formation.

Figure 3:
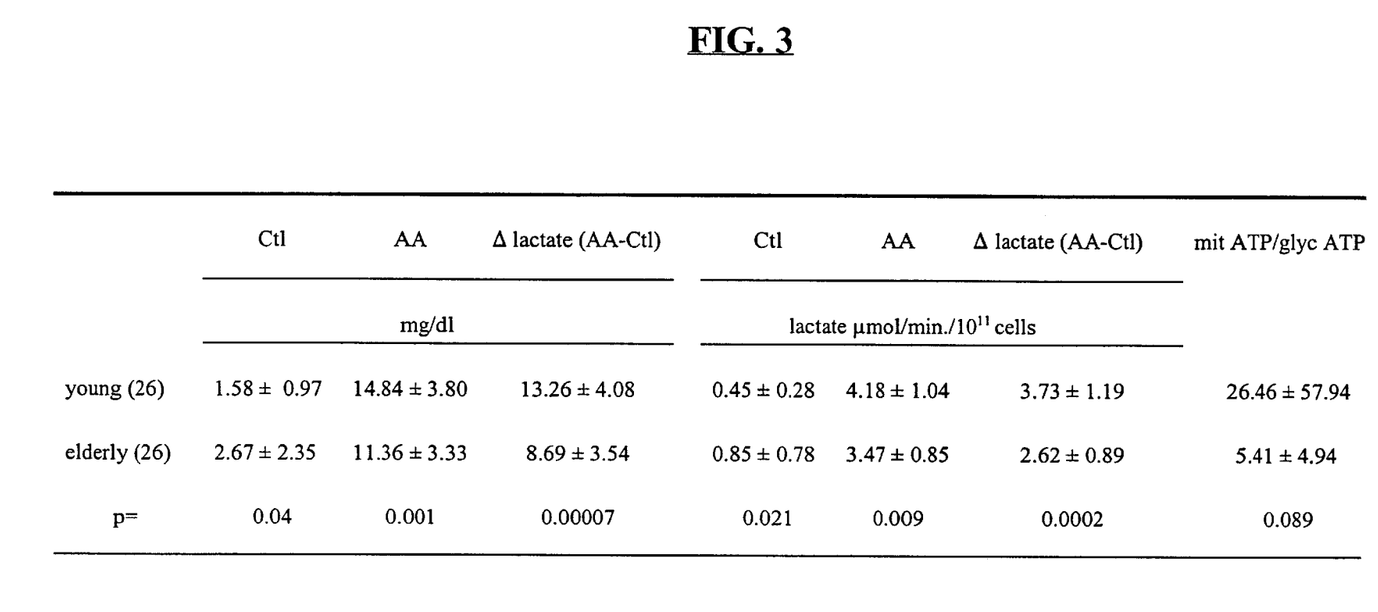
FIG. 3 is a table indicating the production of platelet lactate obtained from young and elderly subjects in the presence of inhibitor AA.

The Applicant conducted a study on two platelet populations incubated for 3 hours and washed, obtained from 26 young subjects (aged 19–30) and 26 elderly subjects (aged 67–87). The data in FIG. 3 reveals the following differences:

a) basic lactate production is higher in the elderly subjects (see Ctl=0.85 compared with Ctl=0.45);
b) lactate production in the presence of antimycin A is slightly lower in the elderly subjects (see AA=4.18 compared with AA=3.47);
c) the Δ lactate value is significantly lower for the elderly than for the young, with p=0.0002;
d) the mitochondrial ATP/glycolytic ATP ratio is also significantly lower for the elderly.

Figure 4:
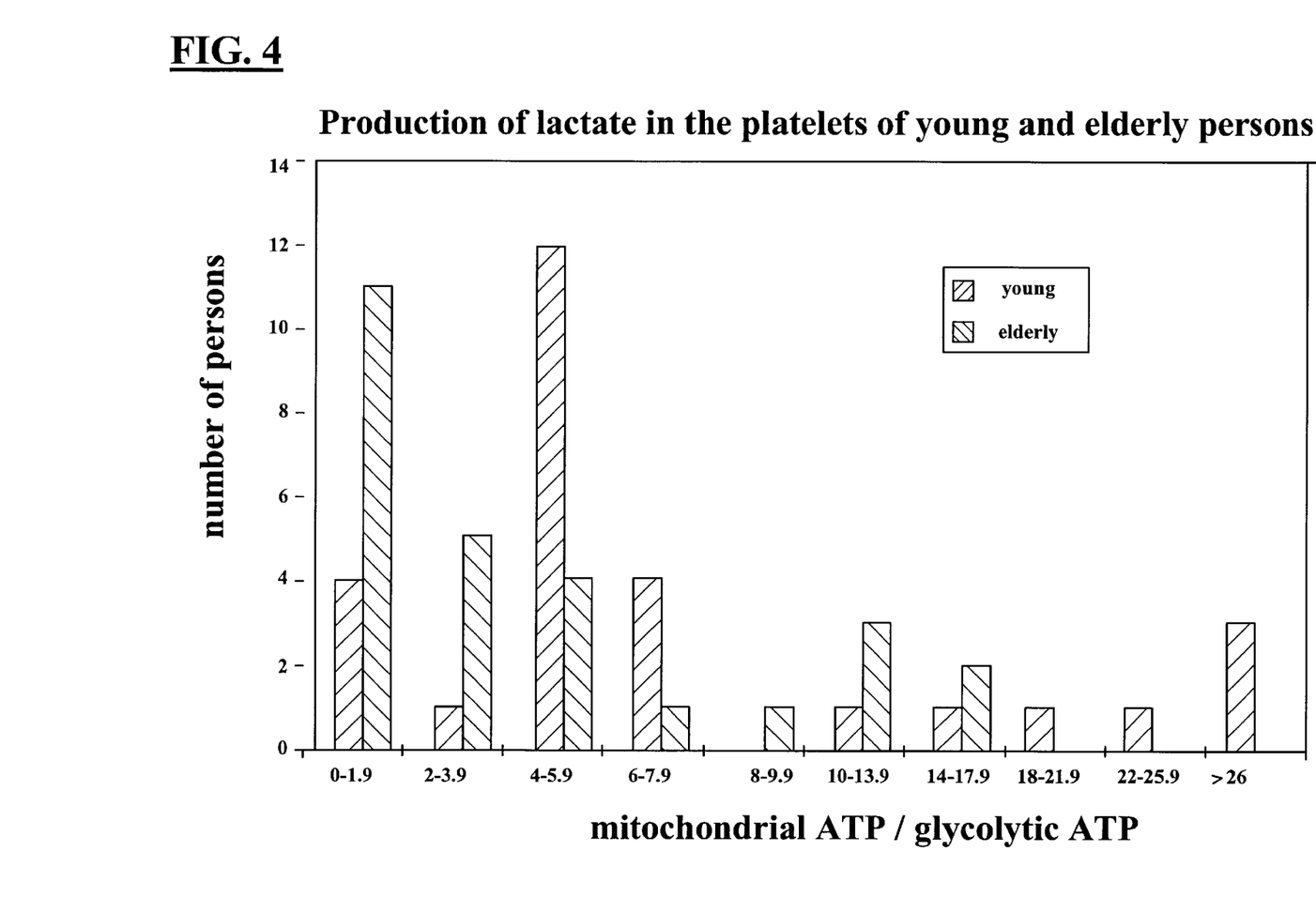
FIG. 4 is a graph of the production of lactate in the platelets of young and elderly individuals.

The results are illustrated in FIG. 4 as the percentage distribution of the Δ lactate values and the mitochondrial ATP/glycolytic ATP ratio. The values for both parameters are clearly lower for the elderly subjects.

The method for measuring mitochondrial activity by measuring platelet Δ lactate which is the subject matter of the present invention can clearly be reproduced and does not involve any significant obstacles. The data indicated reveals that in the platelets of the elderly subjects, ATP synthesis by mitochondrial oxidative phosphorylation falls significantly relative to synthesis at the glycolysis level. The Applicant proposes the method for measuring mitochondrial activity as a biomarker of the mitochondrial activity of the entire organism, based on the theory that the bioenergy in platelets adequately represents the bioenergy of all cells. It may, therefore, be assumed that the alteration in the platelets discovered by the Applicant reflects similar alterations in the various tissues. Therefore, the possibility of measuring a mitochondrial lesion using blood cells which are easily obtained offers an excellent individual biomarker for mitochondrial activity.

The determination proposed by the Applicant is irrespective of the site of the alternation in the oxidative phosphorylation system, since it is based on an evaluation of the total mitochondrial ATP energy yield. This means that the method is versatile and can recognise mitochondrial alterations of various origins which lead to a reduction in ATP synthesis. The Applicant intends to use this biomarker in pathologies in which a mitochondrial alteration has been confirmed or is suspected, that is to say, in degenerative illnesses associated with ageing and in mitochondrial genetic illnesses. Moreover, this determination could also be used to evaluate specific platelet activity, for example, in bags of blood for use in transfusions.

Example of Platelet Lactate Measurement

The measurement was taken using a blood sample from one person.

The platelets, separated and washed as described above, were incubated without the inhibitor antimycin A (AA) (Ctrl) and with the inhibitor antimycin A (AA), and the lactate production was measured at various intervals (30–60–90–120–150 up to 180 minutes).

Figure 5:
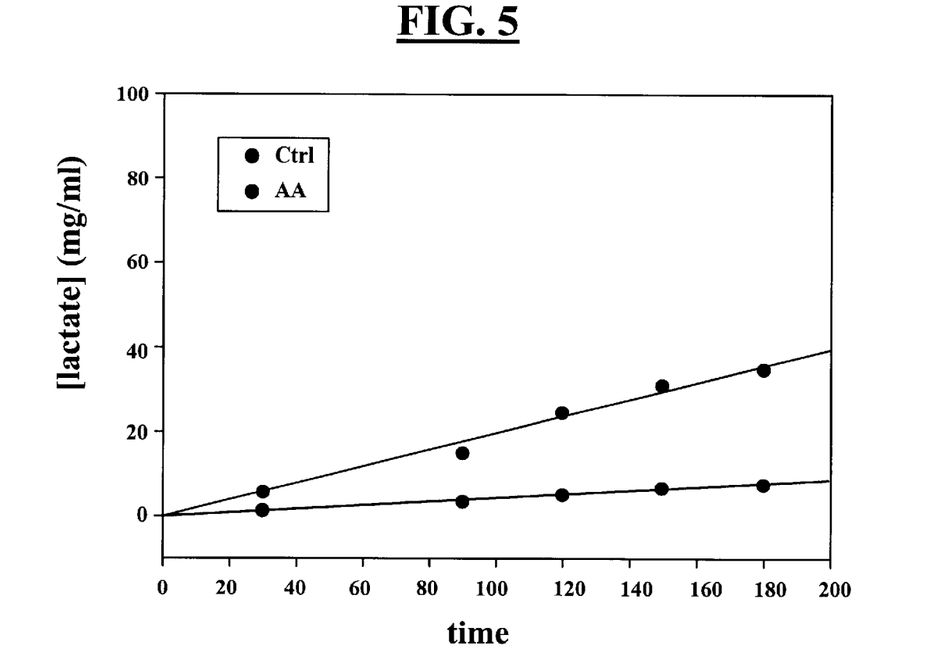
FIG. 5 is a graph of the trend, over time, of lactate production with $50 \times 10^6$ platelets.
Figure 6:
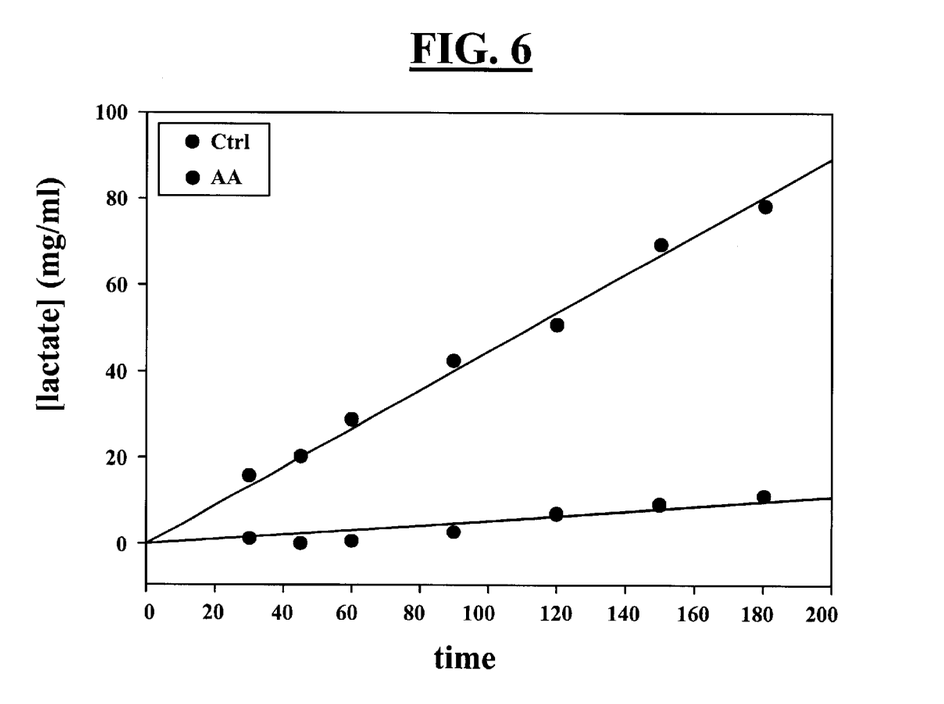
FIG. 6 is a graph of the trend, over time, of lactate production with $100 \times 10^6$ platelets.
Figure 7A:
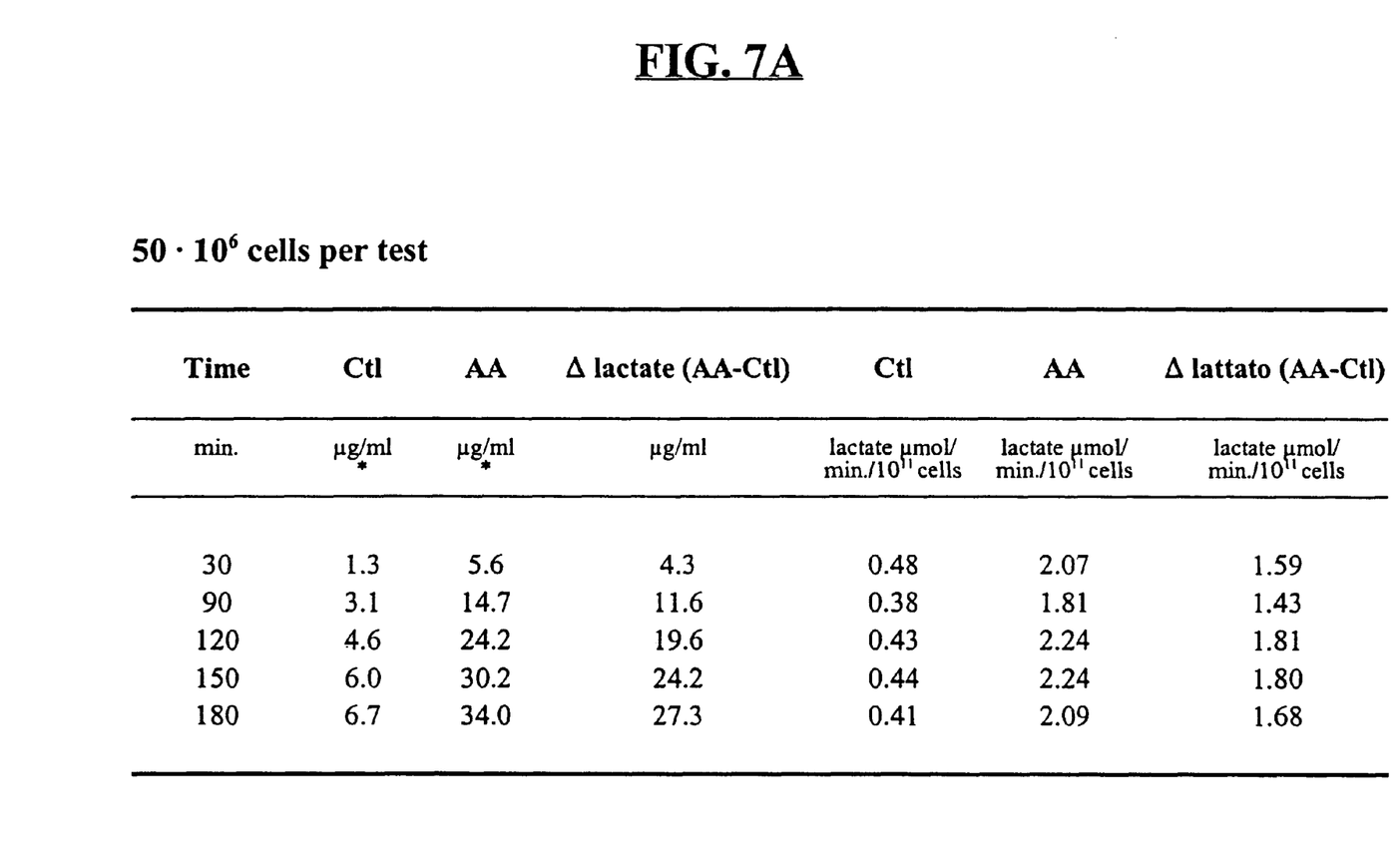
FIG. 7A is a table of lactate production in $50 \times 10^6$ platelets.
Figure 7B:
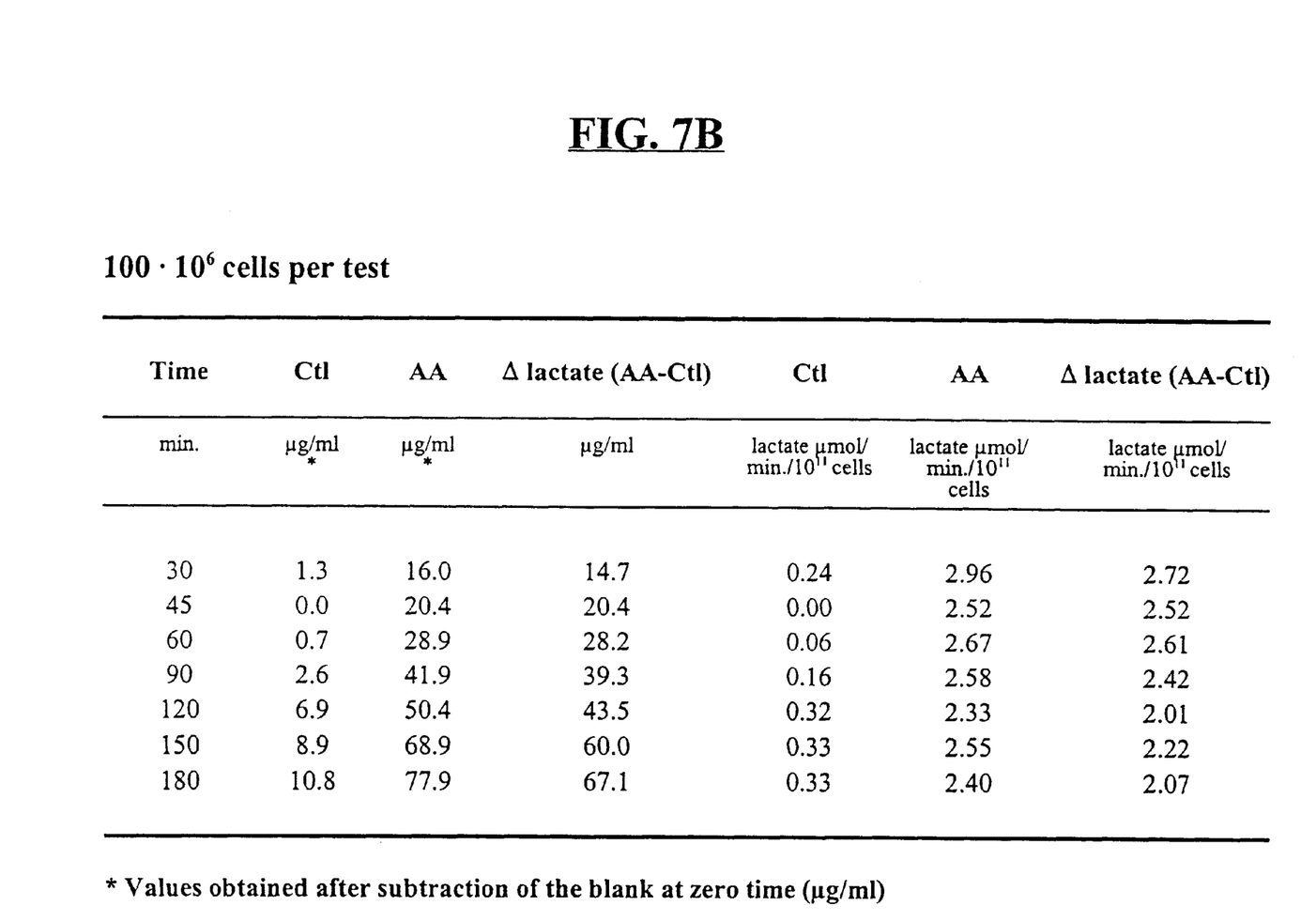
FIG. 7B is a table of lactate production in $100 \times 10^6$ platelets.

The tests were carried out using:
- 50 million cells (platelets) for each test; the data is shown in FIGS. 5 and 7A.
- 100 million cells (platelets) for each test; the data is shown in FIGS. 6 and 7B.

The experiment confirms that the results can be reproduced:
a) using half the amount of platelets, so as to halve the amount of blood taken from the patients (from 20 ml to 10 ml) and, consequently, the material to pour from the bags;
b) using an incubation time of less than the 3 hours in the previous study, in accordance with the usual analysis laboratory requirements.

For greater sensitivity, due to the low lactate concentrations produced in short periods of time by a relatively lower number of platelets, the method for measuring lactate which is the subject matter of the present invention was used.

All stages of isolating and washing the platelets were carried out at 10–37° C. to prevent ultra-structural cell changes associated with freezing. To prevent platelet aggregation, all operations involved the use of silicone glass or plastic laboratory equipment.

Taking Blood 34 ml of blood was taken from the donor, at rest and not subject to pharmacological treatment, using a syringe containing 6 ml of citric acid and trisodium citrate.

The platelets were prepared and washed as described above.

Parts of the platelet suspensions ($100.10^6/500$ μl and $50.10^6/500$ μl) were incubated in a water bath with thermostat control at 37° C. without antimycin A (control) and with antimycin A (20 μg/sample).

In the various tests, the incubation was stopped after 0, 30, 45, 60, 90, 120, 150, 180 minutes, centrifuging at 2240 g for 10 minutes. The supernatants, containing the lactate produced by the platelets, were kept at minus 80° C. until the moment of dosing.

Dosing the lactate

The method for measuring the amount of lactate which forms the subject matter of the present invention is spectrophotometric and is based on the following reaction:

$$\text{Lactate} + \text{3-acetyl-pyridine-NAD}^+ \xrightarrow{\text{LDH}} \text{Pyruvate} + \text{3-acetyl-pyridine-NADH} + \text{H}^+$$

The enzyme LDH used is preferably ox heart. For lactate dosing, the 363 nm absorbance variations are followed, this being the wavelength at which the 3-acetyl-pyridine-NADH has $\epsilon = 9.1$ mM$^{-1}$ cm$^-$.

For dosing, carried out directly in the spectrophotometer bowl, the 0.8 ml of 0.01 M pH 9.20 borate buffer is supplemented with 0.1 ml of 3-acetylpyridine-NAD$^+$ (20 mg/ml), 1 ml of supernatant and 0.01 ml of lactate dehydrogenase (LDH 5 mg/ml).

After 5 minutes the absorbance at 363 nm was read against a blank which did not contain the LDH enzyme solution.

The lactate concentration was calculated using two calibration curves: 0–15 μg of lactate/ml and 15–50 μg of lactate/ml. See FIGS. 5 and 6.

The two curves were used appropriately, depending on the lactate concentration in the samples.

FIGS. 5, 6, 7A and 7B show the lactate production trend over time for the two cell concentrations ($50 \times 10^6$ and $100 \times 10^6$), without antimycin A (AA) (Ctrl) and with antimycin A (AA). The lactate production trend is linear in all cases considered. In particular, there is a similarity between the two straight lines representing the trend of the controls and the two straight lines relative to the samples treated with antimycin A, meaning that the differential values at each time interval (Δ lactate) are reproducible.

It may, therefore, be said that the Δ lactate value is representative of mitochondrial activity.

The preparations containing $50.10^6$ platelets show an appropriate lactate production which is around 50% lower than that of the preparations containing twice the number of platelets. This result indicates that the test can be implemented in a satisfactory fashion even using the platelets from a blood sample with a volume of just 10 ml.

Moreover, given the linearity of the trends and the great sensitivity of the method, incubation may be stopped after only 60 minutes, thus cutting the time required for this analytical stage by two thirds.

On the other hand, when a large number of platelets are available in a small volume, as is the case with bags for transfusions (buffy coats), the incubation time could be further reduced.

The method perfected provides the means for dosing the lactate in a reproducible manner at two intervals with low concentrations (0–15 μg/ml and 15–50 μg/ml) using two calibration curves. The methods commonly used and the kits on sale are not good at reproducing results with low concentrations.

Optimising the procedure could consist in dosing during the various stages, during incubation in the test tubes in which the spectrophotometric reading is taken to measure the lactate, thus simplifying the analyst's work.

Another aim of the present invention is to provide a kit (micromethod) for measuring mitochondrial activity. This kit consists of a pack with two containers. The first container A holds the reagents and materials necessary for washing and incubating the platelets. The second container B holds the reagents and materials required for measuring the quantity (dosing) of the lactate. For example, a platelet mitochondrial activity kit (micromethod) pack for carrying out 100 tests comprises:

Washing and incubating the platelets
(container A)
a) 1 sealed, sterile bottle containing 200 ml of buffer for washing the platelets, with the following composition:
0.12 M NaCl;
0.03 M pH 7.4 Tris/HCl;

3 mM Na-EDTA;

5 mM glucose;

b) 1 sealed dark glass bottle containing 1 mg antimycin powder to be suspended in 100 μl of absolute ethanol. Dosina the lactic acid (container B)

a) 100×1 ml plastic bowls for the spectrophotometer;

b) 4 sealed bottles, each containing 50 mg of 3-acetyl-pyridine-NAD$^+$ to be suspended in 2.5 ml of bidistilled H$_2$O;

c) 1 bottle containing 1.5 ml of ox heart LDH enzyme in 5 mg/ml ammonium sulphate;

d) 1 bottle of 0.01 M pH 9.2 sodium-borate buffer. The kit must be kept at a temperature of 4° C.

What is claimed is:

1. A method for measuring mitochondrial activity by measuring platelet Δ lactate comprising the following stages, not necessarily in succession:

a) separating a platelet-rich plasma from a blood sample;

b) incubating the platelet-rich plasma obtained during the previous stage a) in the presence of inhibitor agents;

c) incubating the platelet-rich plasma obtained during the previous stage a) in the absence of inhibitor agents;

d) separating the lactate produced by the platelets, during incubation stages b) and c) from the platelet-rich plasma;

e) dosing the lactates obtained during stage d);

f) measuring the platelet Δ lactate as the difference between the values obtained from the doses in stage e).

2. The method according to claim 1, comprising at least one wash for the platelets after the separation in stage a) and before the incubation in stages b) and c).

3. The method according to claim 2, wherein the platelet wash is followed by a separation before the incubation in stages b) and c).

4. The method according to claim 1, wherein the doses of lactates obtained from stage d) are a given quantity and envisage the use of the chromogenic agent 3-acetyl-pyridine-NAD$^+$ and the ox heart LDH enzyme.

5. The method according to claim 1, comprising at least one platelet wash following the separation during stage a) and before the incubation during stages b) and c), wherein the doses of stage e) envisage the use of the chromogenic agent 3-acetyl-pyridine-NAD$^+$ and the ox heart LDH enzyme.

6. The method according to claim 1, wherein the doses of stage e) comply with the following stoichiometric reaction:

Lactate+3-acetyl-pyridine-NAD$^+$→Pyruvate+3-acetyl-pyridine-NADH+H$^+$.

7. The method according to claim 1, wherein the inhibitor agents are specific respiratory chain inhibitors and are selected from rotenone, potassium cyanide, antimycin A, oligomycin.

8. The method according to claim 7, wherein the specific respiratory chain inhibitor is antimycin A.

9. The method according to claim 1, wherein the inhibitor agent is a specific glycolysis inhibitor and is deoxyglucose (DOG).

10. The method according to claim 1, wherein the platelet Δ lactate provides an indication of the amount of glycolytic ATP and mitochondrial ATP in the platelets.

11. The method according to claim 1, wherein the incubation during stages b) and c) is carried out at a temperature of between 25 and 40° C. for between 2 and 4 hours.

12. The method according to claim 1, applied as a biomarker for measuring mitochondrial activity so as to detect mitochondrial lesions at cellular level.

13. The method according to claim 12, applied as a biomarker in pathologies in which mitochondrial alterations have been confirmed or are suspected, degenerative illnesses associated with ageing or mitochondrial genetic illnesses.

14. The method according to claim 12, applied so as to evaluate platelet activity in bags of blood.

15. A kit for measuring mitochondrial activity by measuring platelet Δ lactate using a method comprising the following stages, not necessarily in succession:

a) separating a platelet-rich plasma from a blood sample;

b) incubating the platelet-rich plasma obtained during the previous stage a) in the presence of inhibitor agents;

c) incubating the platelet-rich plasma obtained during the previous stage a) in the absence of inhibitor agents;

d) separating the lactate produced by the platelets, during incubation stages b) and c) from the platelet-rich plasma;

e) dosing the lactate obtained during stage d);

f) measuring the platelet Δ lactate as the difference between the values obtained from the doses in stage e), the kit comprising two containers:

a container A holding materials for washing and incubating the platelets, including a washing buffer and the specific inhibitor agent;

a container B holding materials for measuring the quantity of lactate, including spectrophotometer bowls, a chromogenic reagent, an enzyme and a buffer.

16. The kit according to claim 15, wherein the washing buffer in container A comprises NaCl, Tris/HCl pH 7.4, Na-EDTA and glucose.

17. The kit according to claim 15, wherein the specific inhibitor agent is antimycin A.

18. The kit according to claim 15, wherein the chromogenic reagent is 3-acetyl-pyridine-NAD$^+$.

19. The kit according to claim 15, wherein the LDH enzyme is ox heart.

20. The kit according to claim 15, wherein the buffer in container B is a sodium-borate buffer.

* * * * *